United States Patent
McGoogan

[19]

[11] Patent Number: 5,904,140
[45] Date of Patent: May 18, 1999

[54] MEDICAL PACIFIER

[76] Inventor: Elizabeth M. McGoogan, 765 SW. Wisper Bay Dr., Palm City, Fla. 34990

[21] Appl. No.: 08/881,684

[22] Filed: Jun. 24, 1997

[51] Int. Cl.$^6$ ................................................ A61M 15/00
[52] U.S. Cl. .............................. 128/200.24; 128/202.16; 128/203.12; 128/206.24
[58] Field of Search ........................ 128/200.24, 206.29, 128/202.16, 203.12, 200.16

[56] References Cited

U.S. PATENT DOCUMENTS

| | | | |
|---|---|---|---|
| D. 288,126 | 2/1987 | Haupt | D24/45 |
| D. 338,732 | 8/1993 | Maradey-Collazo | D24/194 |
| 2,889,829 | 6/1959 | Tannenbaum et al. | 128/252 |
| 3,037,501 | 6/1962 | Miller | 128/206.29 |
| 3,091,236 | 5/1963 | Delbert | 128/206.29 |
| 4,403,613 | 9/1983 | Panicci . | |
| 4,475,559 | 10/1984 | Horn | 128/200.24 |
| 4,520,809 | 6/1985 | de Greef et al. | 128/200.24 |
| 4,669,461 | 6/1987 | Battaglia et al. | 128/200.24 |
| 4,886,055 | 12/1989 | Hoppough | 128/203.12 |
| 5,123,915 | 6/1992 | Miller et al. | 606/234 |
| 5,462,050 | 10/1995 | Dahlstrand | 128/206.29 |

FOREIGN PATENT DOCUMENTS

| | | | |
|---|---|---|---|
| 1.120.990 | 7/1956 | France | 606/234 |

OTHER PUBLICATIONS

"A New Baby's Comforter," (handwritten date Dec. 4, 1986).

*Primary Examiner*—Aaron J. Lewis
*Attorney, Agent, or Firm*—Holland & Knight LLP

[57] ABSTRACT

A medical pacifier is provided comprising a tubular body including a wall defining a hollow interior having an inlet connected to a nebulizer to receive air-entrained medication, and a closed end mounted to a stopper which carries a nipple. The wall is formed with a discharge port over which a deflector is mounted so that when the air-entrained medication exits from the hollow interior of the body through the discharge port it is directed by the deflector toward the nostrils of an infant sucking on the nipple.

9 Claims, 1 Drawing Sheet

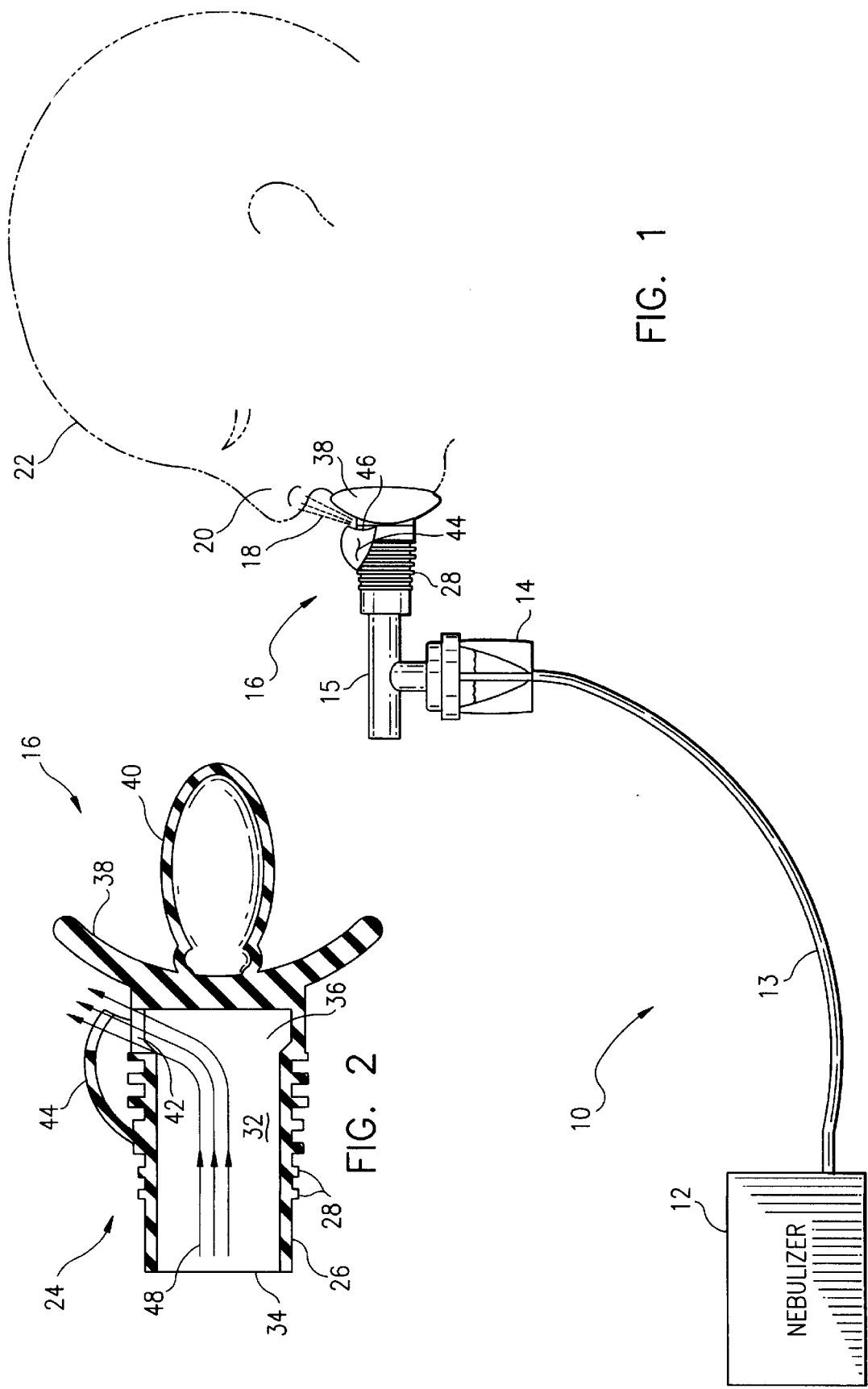

MEDICAL PACIFIER

FIELD OF THE INVENTION

This invention relates to an apparatus for the delivery of medication to a child, and, more particularly, to a medical pacifier which is effective to direct air-entrained medication into the nostrils of a child when the nipple of the pacifier is held in the child's mouth.

BACKGROUND OF THE INVENTION

The use of inhaled medications has increased substantially in recent years, particularly for the treatment of patients with asthma and other illnesses which result in bronchospasm. This is primarily due to the fact that inhalation therapy provides a more efficient utilization of the medication by the body, resulting in decreased dosage requirements for the same results. The efficiency arises from the fact that the medication does not need to travel systematically through the body before it reaches the lungs where it is needed. In patients with conditions such as asthma, such treatment not only is effective but very helpful in preventing acute episodes which has important implications for decreasing admissions to the hospital for asthmatic patients.

Inhaled medications such as bronchodilators and anti-inflammatories are typically dispensed by nebulization or inhalers. Standard inhalers are convenient to use and portable, but require coordination by the user to release the medication and inhale simultaneously. Nebulizers comprise a vapor or mist delivery tube connected to a nebulizer chamber containing medication. The medication is entrained in the vapor stream and inhaled by the patient through a mouthpiece held in position by hand.

A number of difficulties arise in the treatment of toddlers or infants with inhaled medications. Inhalers are not an option because of the coordination needed to dispense the medication and inhale simultaneously. Although nebulization can be effective, it is often a problem to control a toddler or infant who is ill and upset in order to introduce the medication. Children of this age tend to be nose breathers, and it is difficult to hold a mouthpiece in place and get them to breath through the mouth to inhale the medication. It has been found that the use of face masks with toddlers or infants is even more problematic. The mask tends to increase the agitation of the child because it is unfamiliar, and the parent or other attendant becomes reluctant to continue with the treatment due to the adverse reaction of the child.

SUMMARY OF THE INVENTION

It is therefore among the objectives of this invention to provide a medication delivery system for infants and young children which efficiently delivers medication to the child, which requires decreased dosage, which is comfortable and familiar for the infant to use and which may allow for reduced patient monitoring.

These objectives are accomplished in a medical pacifier comprising a tubular body including a wall defining a hollow interior having an inlet connected to the delivery tube of a nebulizer to receive air-entrained medication, and a closed end mounted to a stopper which carries a nipple. The wall is formed with a discharge port over which a deflector is mounted so that when the air-entrained medication exits from the hollow interior of the body through the discharge port it is directed by the deflector toward the nostrils of an infant sucking on the nipple.

This invention is predicated on the concept of employing a conventional nebulizer machine in such a way that the mist or air-entrained medication it produces is efficiently and effectively delivered to the lungs of an infant or small child. The medical pacifier herein relies on the natural sucking urge of the child to retain the device in position while the mist transmitted into the tubular body of the device is directed toward the child's nostrils as it escapes from the discharge port therein.

A number of advantages are obtained by the use of the medical pacifier of this invention. Importantly, because the medical pacifier herein is a familiar appliance to the infant or toddler, the fear and agitation associated with handheld mouthpieces or face masks employed with other nebulizers is substantially reduced or eliminated. The child tends to relax and retain the medical pacifier in place, allowing for reduced patient monitoring. A full dosage of medication is delivered directly into the nostrils of the patient, who at such young age tend to breath mainly through the nose, and the medication travels directly into the lungs where it is needed. The use of systemic medications can therefore be eliminated, which typically require larger dosages and can create undesirable side effects.

BRIEF DESCRIPTION OF THE DRAWINGS

The structure, operation and advantages of the presently preferred embodiment of this invention will become further apparent upon consideration of the following description, taken in conjunction with the accompanying drawings, wherein:

FIG. 1 is a schematic, perspective view of a nebulizer connected to the medical pacifier of this invention in position within the mouth of an infant; and FIG. 2 is a cross-sectional view of the medical pacifier herein.

DETAILED DESCRIPTION OF THE INVENTION

With reference initially to FIG. 1, a system 10 for transmitting air-entrained medication to a child is diagrammatically illustrated. The system 10 includes a nebulizer 12 which is connected by a delivery tube 13 to a medicine cup 14. The medicine cup 14 has a reservoir adapted to receive medication such as a bronchodilator which is closed by a fitting 15 connected to a medical pacifier 16, described in detail below. The detailed construction and operation of the nebulizer 12 forms no part of this invention and is therefore not described herein. It is contemplated that any suitable commercially available nebulizer 12 could be employed in the system 10 of this invention.

As is well known, the nebulizer 12 is effective to "break up" or entrain medication contained within the medicine cup 14 in a stream of air to form a mist or vapor which can be transmitted to the patient. As discussed more fully below, the air-entrained medication or mist 18 is directed by the medical pacifier 16 herein in a direction toward the nostrils 20 of a child 22 when the pacifier 16 is in the child's mouth.

With reference to FIG. 2, the medical pacifier 16 is illustrated in detail. The pacifier 16 comprises a generally tubular-shaped body 24 having a wall 26 formed with external threads 28. The external threads 28 are sized to mate with the fitting 15 connected to the medicine cup 14 to make a substantially air-tight connection therebetween.

The wall 26 of tubular body 24 defines a hollow interior 32 having an inlet end 34 and an opposite end 36 which is closed by a stopper 38 mounted to a nipple 40. As also seen in FIG. 1, the stopper 38 is generally cup-shaped to rest against the lips of a child 22 when the nipple 40 is inside of the child's mouth.

In the presently preferred embodiment, the pacifier wall 26 is formed with a discharge port 42 adjacent the closed end 36 of the hollow interior 32 and the stopper 38. The axis of the discharge port 42 is oriented substantially perpendicular to the longitudinal axis of the hollow interior 32. A deflector 44 is mounted to the outside of the wall 26 in a position at least partially overlying the discharge port 42. The leading edge 46 of the deflector 44 is preferably tapered in the area where it overlies the discharge port 42.

The operation of the system 10 is as follows. The medical pacifier 16 is attached by the fitting 15 to the medicine cup 14, which, in turn, is connected by the delivery tube 13 to the nebulizer 12. The nebulizer 12 is operated in a conventional manner to form a mist 18 or stream of air-entrained medication within the medicine cup 14 which is transmitted through the fitting 15 into the hollow interior 32 of the pacifier body 24. The air-entrained medication or mist 18 flows through the hollow interior 32 in the direction of the arrows 48 shown in FIG. 2, and when it impacts the stopper 38 the mist 18 is forced through the discharge port 42 formed in the wall 26. The shape and positioning of deflector 44 directs the mist 18 toward the nostrils 20 of the child 22 so that the airborne medication can be inhaled by normal breathing. The discharge port 42 and deflector 44 are properly positioned with respect to the child's nostrils 20 with the nipple 40 inserted within the child's mouth as he or she sucks on the nipple. See FIG. 1. Entry of the airborne medication into the nostrils and lungs of the child is aided by both the natural suction created during inhalation, and a positive pressure on the air-entrained medication or mist 18.

While the invention has been described with reference to a preferred embodiment, it should be understood by those skilled in the art that various changes may be made and equivalents may be substituted for the elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A method of delivering medication to a child, comprising:

providing a medical pacifier having a body formed with a hollow interior, a nipple located at one end of the body, a discharge port formed in the body in communication with the hollow interior for discharging air-entrained medication from the hollow interior and a deflector mounted on the exterior of the body proximate to the discharge port;

transmitting air-entrained medication into the interior of the medical pacifier;

directing the air-entrained medication from the interior of the medical pacifier, through the discharge port and into engagement with the deflector so that the air-entrained medication is directed into the nostrils of a child with the nipple held in such a child's mouth.

2. Apparatus for the delivery of air-entrained medication to a child, comprising:

a body formed with a wall defining a hollow interior having an inlet end connectable to a source of air-entrained medication and a closed end, said wall being formed with a discharge port;

a stopper connected to said closed end of said hollow interior, and a nipple protruding from said stopper, said nipple being adapted to be held within a child's mouth so that the stopper rests against such a child's lips;

a deflector carried by said wall in a position to direct air-entrained medication exiting said discharge port of said body in a direction toward a child's nostrils when said nipple is held in such a child's mouth.

3. The apparatus of claim 2 in which said discharge port is formed in said wall of said body adjacent said closed end of said hollow interior.

4. The apparatus of claim 2 in which said hollow interior of said body has a longitudinal axis, and said discharge port has a longitudinal axis which is substantially perpendicular to said longitudinal axis of said hollow interior.

5. The apparatus of claim 2 in which said deflector is a generally cup-shaped element which at least partially covers said discharge port.

6. Apparatus for the delivery of air-entrained medication to a child, comprising:

a nebulizer which is effective to produce a stream of air-entrained medication;

a medical pacifier, including:

(i) a body formed with a wall defining a hollow interior having an inlet end connected to said nebulizer and a closed end, said wall being formed with a discharge port;

(ii) a stopper connected to said closed end of said body interior, and a nipple protruding from said stopper, said nipple being adapted to be held within a child's mouth so that the stopper rests against such a child's lips;

(iii) a deflector carried by said wall in a position to direct air-entrained medication exiting said discharge port of said body in a direction toward a child's nostrils when said nipple is held in such a child's mouth.

7. The apparatus of claim 6 in which said discharge port is formed in said wall of said body adjacent said closed end of said hollow interior.

8. The apparatus of claim 6 in which said hollow interior of said body has a longitudinal axis, and said discharge port has a longitudinal axis which is substantially perpendicular to said longitudinal axis of said hollow interior.

9. The apparatus of claim 6 in which said deflector is a generally cup-shaped element which at least partially covers said discharge port.

* * * * *